United States Patent [19]

Keilman

[11] Patent Number: 4,475,376

[45] Date of Patent: Oct. 9, 1984

[54] APPARATUS FOR TESTING ULTRASONIC TRANSDUCERS

[75] Inventor: George W. Keilman, Seattle, Wash.

[73] Assignee: Advanced Technology Laboratories, Inc., Bellevue, Wash.

[21] Appl. No.: 445,795

[22] Filed: Dec. 1, 1982

[51] Int. Cl.³ .................... G01N 29/00; H04R 29/00
[52] U.S. Cl. ........................................ 73/1 DV; 367/13
[58] Field of Search .................... 73/1 DV, 642, 644; 367/13

[56] References Cited

U.S. PATENT DOCUMENTS 3,529,465  9/1970  Kleesattel et al. .................... 73/644

FOREIGN PATENT DOCUMENTS 732083  6/1955  United Kingdom .................. 73/644

*Primary Examiner*—James J. Gill
*Attorney, Agent, or Firm*—Lawrence S. Levinson; Sanford J. Asman

[57] ABSTRACT

A probe for testing ultrasound transducers is described. The probe is made of a body of material which absorbs ultrasound. There is a conical opening in the body, and a spherical transducer is mounted in the wider opening at the base of the conical opening. When the probe is used as a surface probe, a transducer undergoing tests is placed at the opening at the apex of the cone. Typically the conical opening is filled with a fluid which simulates the absorption qualities of the material with which the tested transducer will ultimately be used. For example, the transducer undergoing the test will be used with human body tissue, so a fluid such as water or light mineral oil would typically fill the cone-shaped opening. The present invention can also be used as a hydrophone, because of the manner in which it generates, or senses, pressure waves at a point in space.

12 Claims, 1 Drawing Figure

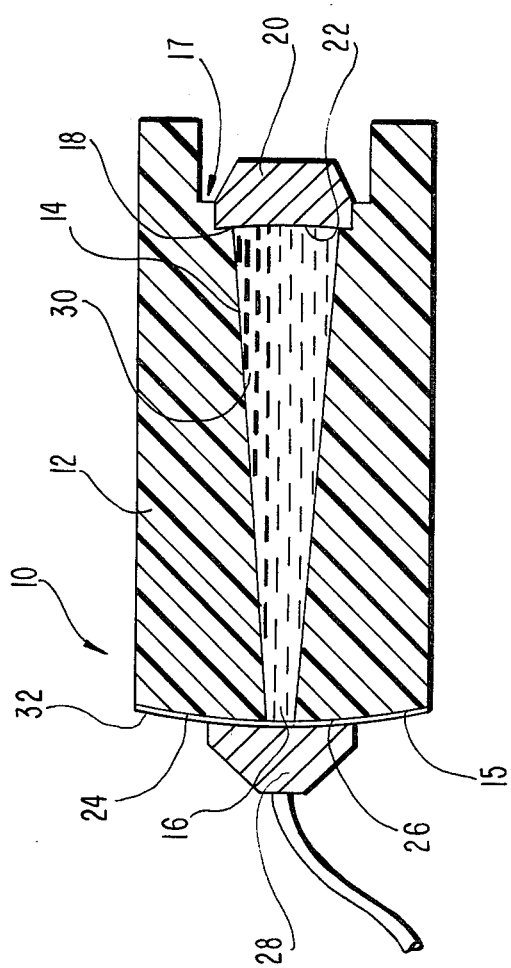

APPARATUS FOR TESTING ULTRASONIC TRANSDUCERS

BACKGROUND OF THE INVENTION

The present invention relates to an apparatus used to test ultrasound transducers. In particular, the device is used to test ultrasound transducers of the type used in medical ultrasound diagnostic equipment.

Ultrasonic transducers are used in the manufacture of scanheads for ultrasonic diagnostic equipment. In a typical ultrasonic diagnostic scanhead, three ultrasonic transducers are used to transmit the ultrasound and to sense the echos used to form the image. The present state of the art in electronics has advanced to the point where a factor limiting improvements in ultrasound units is the ability to match the three transducers used in a single scanhead. If the transducers are not of uniformly high quality, the image will appear to flicker due to differences between the transducers. Unfortunately, it is difficult to characterize transducers in order to match them. Therefore, it is very difficult to get matched transducers. Accordingly, it would be desirable to be able to characterize transducers over their entire surface as well as any point in the acoustic field in order that matched transducers could be placed into a particular scanhead. A device capable of testing transducers could also be used to improve yields and determine the effects which create problems in their manufacture.

Similar types of problems arise in the manufacture of a linear array and phased array transducers. Yet, heretofore, there has been no way to measure the surface vibrational characteristics of ultrasound transducers which were coupled to a medium of the acoustic impedance used in actual operating conditions, e.g., a medium having an acoustic impedance substantially equal to that of water. Various researchers have used laser interferometers to measure the surface displacement of transducers and generate contour patterns. Such techniques are highly complex, very expensive, and subject to numerous inaccuracies. Likewise, existing miniature hydrophone probes employ extremely small active areas to measure the point response in the acoustic field. This typically results in devices which are extremely fragile, difficult to match electrically, and unreliable. Consequently, manufacturers of ultrasound transducers do not generally use such techniques.

Based upon the present need to properly characterize transducers and the absence of any equipment or methodology adequate to perform that function, it would be highly desirable to have a piece of equipment to evaluate the surface vibration of transducers and measure the acoustic field at any point in space.

SUMMARY OF THE INVENTION

The present invention is a probe which is capable of directing the output of a spherical ultrasound transducer and focusing it down substantially to a point. The probe uses a conical waveguide to maintain a spherical wavefront as the wave propagates from a transducer in the probe toward a point-like opening near the apex of the waveguide. By maintaining spherical wavefronts, the waveguide transforms the probe transducer into a virtual spherical transducer of the same diameter as the point-like opening. A transducer undergoing tests can then be placed at that point, and its response, at that point can be measured and characterized. The principle of operation of the present invention is reciprocal. Accordingly, the transducer undergoing the test can be used as the transmitter, and the probe transducer can be used to measure the output of a point on the surface of the test transducer or the acoustic field at any point in space.

The invention is comprised of a body of material which is highly absorbent of sound waves which pass into it. There is a cone-shaped opening in the body, and a spherical transducer is fixed at the wider opening in the cone-shaped opening. The smaller opening is substantially a point, whereby the apex of the cone is just outside of the body. The cone-shaped opening is filled with a fluid which simulates the acoustic qualities of the material with which the tested transducer will ultimately be used. Typically, the transducer undergoing the test will be used with human tissue, so a fluid, such as water or light mineral oil, would typically fill the cone-shaped opening.

BRIEF DESCRIPTION OF THE DRAWING

The sole FIGURE of the Drawing is a cross-sectional view of the probe of the present invention.

DETAILED DESCRIPTION OF THE PREFERRED EMBODIMENT

Referring to the FIGURE, a preferred embodiment of the probe 10 of the present invention, used as a surface probe, comprises a body 12 of material having a conical cavity 14 formed therein. At one end 15 there is a small diameter opening 16, and at the other end there is a substantially larger diameter opening 18. A probe transducer 20 is fitted into the body 12 such that it fully covers the large opening 18. The probe transducer 20 is manufactured to have a spherical surface 22, whereby the center of the spherical surface 22 is at the apex of the cone shaped cavity 14, just outside the opening 16. It is important to have the active area of the probe transducer 20 coincide with the opening 18 of the cone shaped cavity 14, so that the spherical wavefront generated by the probe transducer 20 completely fills the cone opening 16. The surface 24 of one end of the body 12 (shown on the left side of the FIGURE) is formed to have a shape which coincides with the surface 26 of a transducer 28 undergoing tests. Thus, a different surface probe 10 would be used to test a transducer 28 having a spherical surface 26 than would be used to test a transducer having a flat surface. These differences will be obvious to those having ordinary skill in the art.

The conical cavity 14 is filled with a fluid 30. It is important that the acoustic impedence of the fluid 30 be approximately equal to the acoustic impedance of the material the body 12 is made of in order that any test procedures which are conducted using the device will exhibit the same characteristics as the device presents. The acoustic impedance of the fluid 30 and the acoustic impedance of the material should also be approximately equal to the acoustic impedance of the ultimate target material which the test transducer 28 will ultimately be used with. Accordingly, in the case of testing ultrasonic transducers of the type used in medical diagnostic equipment, the acoustic impedance of both the body 12 and the fluid 30 should be approximately equal to the acoustic impedance of human tissue, i.e. on the order of 1.5 MegaRayls.

The acoustic impedance is chosen to be close to that of human tissue so that the transducer is tested under conditions close to that in which it is used. It is also important that the spherical wave travelling through the waveguide be totally reflected by the wall of the conical cavity 14. However, the reflection coefficient, gamma, is defined for longitudinal waves, normally incident at an interface, to be equal to the impedance of the body 12 minus the impedance of the fluid 30 divided by the sum of the impedance of the body 12 plus the impedance of the fluid 30. This formula for gamma would imply that gamma would be approximately equal to zero under the condition that the acoustic impedance of the body 12 be equal to the acoustic impedance of the fluid 30. However, the formula for gamma is valid only for waves which are normal to the interface between the body 12 and the fluid 30. In the surface probe 10 of the present invention, the waves which propagate through the cone shaped cavity 14 propagate in a direction which is substantially parallel to the interface. Accordingly, the waves which propagate through the cone shaped cavity 14 can be made to be beyond the "critical angle" which would insure that there was total internal reflection of the waves inside the cone shaped cavity 14. The "critical angle" is defined to be the arcsin of the velocity of the fluid 30 divided by the velocity of the body. Thus, by choosing a material for the body 12 which has a propagation velocity which is higher than the propagation velocity of the fluid 30, it is not terribly critical how much higher the propagation velocity of the body material be than the fluid material in view of the fact that the wave propagation is almost parallel to the interface surface.

Two additional factors help in the selection of materials for the body 12 and the fluid 30. First of all, it is desirable to have the attenuation of sound within the body 12 be as high as possible, while at the same time the attenuation of sound propagating through the fluid 30 should be as low as possible. Thus, any stray sound which passes through the interface into the body 12 would not measurably affect the test.

In addition to the foregoing acoustic qualities of the fluid 30, it is also important that the body 12 be made of mechanically, chemically stable material which does not outgas after it has been shaped. Similarly, it is important that the fluid 30 does not outgas and that the fluid 30 be chemically stable in the probe environment. Also, the fluid 30 should not have any qualities which would deteriorate the body 12.

In view of the above criteria, a number of possible fluids can be selected. These include air, water, light mineral oil, or silicone fluid. The body 12 is preferably made of a material such as a urethane or a filled silicone. In the preferred embodiment of the invention, the body 12 is cast using a urethane material, such as Conap EN-4 urethane.

The size of the opening 16 should be relatively small, i.e. on the order of one wave length of the frequency of the transducer 28 under test. The frequency response of the probe transducer 20 should be as broad band as possible in order that the probe transducer 20 not affect the measurements.

In using the surface probe 10 one would move the test transducer 28 over the surface 24 while measuring the response of the transducer 28. As will be recognized by those skilled in the art, the probe transducer 20 can be used to generate sound, in which case the test transducer 28 would be measured electrically, or, alternatively, the test transducer 28 can be used to produce sound and the electrical output of the probe transducer 20 can be measured. Except for nonlinearities within the fluid 30, the surface probe 10 is completely reciprocal with respect to which transducer 20, 28 excites and which transducer 28, 20 is electrically measured.

In a preferred embodiment of the invention, the surface 24 is covered by a low friction covering, such as Teflon tape, in order to keep the surface slippery so that the test transducer 28 can be moved readily over the surface 24 and also to keep the surface clean as the covering keeps the fluid 30 within the cone shaped cavity 14.

While the preferred embodiment of the invention has been described as a surface probe, used for the surface testing of transducers, it is also desirable to be able to test transducers which are operating in space. Traditionally, a device known as a "hydrophone" is used for this purpose. A hydrophone is a device which is used to measure pressure waves at a point in space or to generate a point source of pressure waves. As will be obvious to those skilled in the art, if the transducer being tested was removed from the surface 24 of the present probe 10, and if the probe 10 was placed into a medium which had an acoustic impedance which matched that of the acoustic impedance of the fluid 30 within the cavity 14, then the probe 10 could be used as a hydrophone. If the probe 10 is used as a hydrophone, then it is not necessary for the body 12 to be made of a material which is acoustically matched to the fluid 30. The body 12 should be made of a material which has a higher acoustic impedance than the fluid 30 in order to insure that there will be a positive reflection coefficient for spherical waves. Accordingly, if the probe 10 is used as a hydrophone, then the body can be made of a material other than urethane, such as a metal or other high impedance material.

I claim:

1. A probe for testing ultrasonic transducers comprising:
   (a) a body of material having a cone-shaped cavity formed therein, said cone-shaped cavity having a wide opening adjacent one end of said body and a narrow opening adjacent the other end of said body;
   (b) an ultrasound transducer having a spherical surface, said ultrasound transducer being mounted in the wider one of said openings and oriented to transmit, or receive, ultrasound waves toward, or from said narrow opening, said narrow opening being substantially at the apex of said spherical surface and the walls of said cone-shaped cavity connecting said wide opening to said narrow opening; and
   (c) a fluid medium within said cone-shaped opening, said fluid medium being capable of passing ultrasound waves therethrough.

2. The probe of claim 1 wherein said body is comprised of a material which is absorbent to ultrasonic energy.

3. The probe of claim 1 wherein said fluid medium is contained within said cavity by said spherical ultrasound transducer at one end and by a covering over said narrow opening at the other end.

4. The probe of claim 1 wherein the end of said body which is adjacent to said narrow opening of said cavity is formed to have a surface with a shape that complements the shape of the transducer which is to be tested.

5. The probe of claim 4 wherein said surface of said body which complements the shape of the transducer which is to be tested is covered by a low friction material.

6. The probe of claim 5 wherein said low friction material is a fluoroelastomer such as Teflon.

7. The probe of claim 1 wherein said body is made of a material which has an acoustic impedance substantially equal to that of the material which with the tested transducer will ultimately be used.

8. The probe of claim 7 wherein said body is made of a urethane material.

9. The probe of claim 7 wherein said tested transducer will be used with human tissue and said fluid medium is selected to have an acoustic impedance substantially equal to that of human tissue.

10. the probe of claim 9 wherein said fluid medium is selected from the group consisting of air, water, and mineral oil.

11. The probe of claim 1 wherein said body is made of a material which has an acoustic impedance higher than that of said fluid medium.

12. The probe of claim 9 wherein said body is made of a metal.

* * * * *